US010111813B2

(12) United States Patent
Samain et al.

(10) Patent No.: US 10,111,813 B2
(45) Date of Patent: Oct. 30, 2018

(54) OXIDATION DYEING PROCESS USING A SUBSTRATE BEARING AT LEAST ONE OXIDATION DYE AND AN AQUEOUS COMPOSITION

(71) Applicant: L'OREAL, Paris (FR)

(72) Inventors: Henri Samain, Bievres (FR); Géraldine Fack, Levallois-Perret (FR); Delphine Charrier, Boulogne Billancourt (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/108,492

(22) PCT Filed: Dec. 29, 2014

(86) PCT No.: PCT/EP2014/079394
§ 371 (c)(1),
(2) Date: Jun. 27, 2016

(87) PCT Pub. No.: WO2015/097307
PCT Pub. Date: Jul. 2, 2015

(65) Prior Publication Data
US 2016/0317399 A1  Nov. 3, 2016

(30) Foreign Application Priority Data
Dec. 27, 2013  (FR) ..................... 13 63655

(51) Int. Cl.
| *A61Q 5/10* | (2006.01) |
| *A61K 8/02* | (2006.01) |
| *B41M 5/025* | (2006.01) |
| *A61K 8/34* | (2006.01) |
| *A61K 8/41* | (2006.01) |
| *B44C 1/165* | (2006.01) |

(52) U.S. Cl.
CPC .......... *A61K 8/0233* (2013.01); *A61K 8/0204* (2013.01); *A61K 8/347* (2013.01); *A61K 8/411* (2013.01); *A61K 8/415* (2013.01); *A61Q 5/10* (2013.01); *B41M 5/025* (2013.01); *B44C 1/165* (2013.01); *A61K 2800/4324* (2013.01)

(58) Field of Classification Search
CPC ........ A61Q 5/10; A61K 8/0204; A61K 8/033; A61K 8/411; A61K 8/415; A61K 8/347; A61K 2800/4324; B44C 1/165
See application file for complete search history.

(56) References Cited

U.S. PATENT DOCUMENTS

| 4,003,699 A | 1/1977 | Rose et al. |
| RE30,199 E | 1/1980 | Rose et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Löwe et al. |
| 5,931,168 A * | 8/1999 | Abercrombie ..... A45D 19/0025 132/208 |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,730,789 B1 | 5/2004 | Birault et al. |
| 2002/0050013 A1 | 5/2002 | Vidal et al. |
| 2003/0019051 A9 | 1/2003 | Vidal et al. |
| 2005/0028302 A1* | 2/2005 | Audousset ............. A61K 8/415 8/405 |
| 2009/0050171 A1* | 2/2009 | Barrass .............. A45D 19/0025 132/208 |
| 2013/0074863 A1 | 3/2013 | Kleen et al. |
| 2014/0352714 A1 | 12/2014 | Samain |

FOREIGN PATENT DOCUMENTS

| DE | 2359399 A1 | 6/1975 |
| DE | 3843892 A1 | 6/1990 |
| DE | 4133951 A1 | 4/1993 |
| DE | 19543988 A1 | 5/1997 |
| EP | 0770375 A1 | 5/1997 |
| FR | 2733749 A1 | 11/1996 |
| FR | 2801308 A1 | 5/2001 |
| FR | 2886136 A1 | 12/2006 |
| FR | 2984087 A1 | 6/2013 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 96/15765 A1 | 5/1996 |
| WO | 03/041531 A1 | 5/2003 |
| WO | WO 2013/093775 A1 * | 6/2013 ............... A61Q 5/10 |
| WO | 2015/097309 A1 | 7/2015 |

OTHER PUBLICATIONS

International Search Report for PCT/EP2014/079394, dated Mar. 17, 2015.
International Search Report for PCT/EP2014/079396, dated Mar. 17, 2015.
PCT/IB/304 Form for PCT/EP2014/079394, mailed Feb. 27, 2015.
PCT/IB/304 Form for PCT/EP2014/079396, mailed Jan. 19, 2015.

* cited by examiner

*Primary Examiner* — Eisa B Elhilo
(74) *Attorney, Agent, or Firm* — The Marbury Law Group, PLLC

(57) ABSTRACT

The present invention relates to the field of dyeing keratin fibers and more particularly to the field of hair dyeing. The present invention relates to a process for the oxidation dyeing of keratin fibers, in particular human keratin fibers such as the hair, which consists in using on the said fibers i) a substrate comprising on its surface one or more oxidation dyes, and ii) an aqueous composition comprising one or more oxidizing agents. The present invention also relates to a process for preparing the said substrate thus pretreated.

17 Claims, No Drawings

OXIDATION DYEING PROCESS USING A SUBSTRATE BEARING AT LEAST ONE OXIDATION DYE AND AN AQUEOUS COMPOSITION

CROSS REFERENCE TO RELATED APPLICATIONS

This is a national stage application of PCT/EP2014/079394, filed internationally on Dec. 29, 2014, which claims priority to French Application No. 1363655, filed on Dec. 27, 2013, both of which are incorporated by reference herein in their entireties.

The present invention relates to the field of dyeing keratin fibres and more particularly to the field of hair dyeing.

The present invention relates to a process for the oxidation dyeing of keratin fibres, in particular human keratin fibres such as the hair, which consists in using on the said fibres i) a substrate comprising on its surface one or more oxidation dyes, and ii) an aqueous composition comprising one or more oxidizing agents.

The present invention also relates to a process for preparing the substrate as described previously, used via a printing method.

The invention also relates to an element in sheet form pretreated with a composition comprising one or more oxidation dyes.

It is known practice to dye keratin fibres, in particular human keratin fibres such as the hair, to obtain "permanent" colourings with dye compositions containing oxidation dye precursors, which are generally known as oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colouring modifiers, the latter being chosen especially from aromatic meta-diamines, meta-aminophenols, meta-diphenols and certain heterocyclic compounds such as indole or pyridine compounds. The variety of molecules used as oxidation bases and couplers allows a wide range of colours to be obtained.

Standard oxidation dyeing processes thus consist generally in applying to keratin fibres a dye composition comprising oxidation bases or a mixture of oxidation bases and couplers with hydrogen peroxide ($H_2O_2$ or aqueous hydrogen peroxide solution), as oxidizing agent, in leaving it to diffuse, and then in rinsing the said fibres. The colourings resulting therefrom are generally permanent, strong and resistant to external agents, especially to light, bad weather, washing, perspiration and rubbing.

However, it has been found that it is often difficult or even impossible to obtain colourings with novel visual results by means of the "standard" oxidation dyeing techniques. In particular, these processes do not satisfactorily afford coloured patterns, which may lead to novel optical effects on the entire head of hair, which are both sharp and precise.

These standard oxidation dyeing processes also have the drawback of staining the hands of the user or of the hair stylist during the application to the hair of the ready-to-use composition resulting from mixing the dye composition and the oxidizing composition. Similarly, this type of process may also give rise to undesirable stains on the user's scalp, contour of the face and/or clothing, which may be due to application errors and/or to problems of running of the compositions.

These standard oxidation dyeing processes also entail the risk of not leading to the final colouring desired by the user because of an error arising during the handling of the dye compositions and oxidizing compositions or because of a poor choice of the starting dye compositions.

It has also been found that the shelf storage of the dye compositions and oxidizing compositions used for obtaining the desired colouring may pose problems of space occupation and/or of storage over the long term, especially in hairstyling salons.

These oxidation dyeing processes may thus prove to be impractical for achieving many varied colours as a function of the different users.

Moreover, it is already known practice from document FR 2 984 087 to use a dyeing or bleaching process which consists in placing keratin fibres in contact with a substrate bearing a bleaching or dye composition having a formulation that changes depending on the position on the said substrate, so as to obtain shaded dyeing or bleaching.

However, the said document does not describe a process that is capable of producing precise patterns and/or of leading to uniform colourings.

There is thus a real need to perform a process for the oxidation dyeing of keratin fibres, in particular of human keratin fibres such as the hair, which does not have the drawbacks mentioned previously, i.e. which is especially capable of giving on the said fibres colourings that may be unified and/or that may have novel visual results, in particular precise coloured patterns, of reducing the problems of space occupation and/or storage of the compositions used, of minimizing the risks of contact that may arise between the compositions used and the user's hands, scalp and/or clothing, and also the risks of not obtaining the desired colouring.

This aim is achieved by the present invention, one subject of which is especially a process for the oxidation dyeing of keratin fibres, in particular human keratin fibres such as the hair, which consists in using on the said fibres i) a substrate comprising on its surface a dye composition comprising one or more oxidation dyes; the said composition being printed onto the surface of the said surface, and ii) an aqueous composition comprising one or more chemical oxidizing agents.

The process for dyeing keratin fibres thus uses a substrate onto which has been deposited one or more oxidation dyes. In other words, the substrate has been pretreated on its surface with a dye composition containing one or more oxidation dyes.

Hence, the oxidation dyes are printed onto the surface of the substrate.

Indeed, the dye composition is printed onto the surface of the substrate.

Thus, in the course of placing the keratin fibres in contact with the pretreated substrate and the aqueous oxidizing composition, the oxidation dyes present on the surface of the substrate dissolve and react with the oxidizing agent, on contact with the said fibres, to dye them, which leads to colourings that may be unified and/or to coloured patterns.

In particular, the oxidation dye(s) are deposited on the surface of the substrate and may be localized in certain places on the said surface so as to represent one or more geometrical forms in order thereafter to produce one or more coloured patterns on the keratin fibres after contact between the said fibres, the pretreated substrate and the aqueous oxidizing composition. In other words, the substrate may be pretreated in places with a dye composition containing one or more oxidation dyes so as to be able to produce one or more coloured patterns on the fibres.

Therefore, the dye composition may be locally printed on the surface of the said substrate.

The dyeing process according to the invention thus makes it possible to produce on the keratin fibres, with great precision, coloured patterns that are visually sharp. In particular, this process makes it possible to produce millimeter-sized coloured patterns having all types of forms, such as spots or waves, which are easily reproducible. These patterns may also lead to novel optical effects when they are then repeated over the entire head of hair.

In other words, the dyeing process according to the invention makes it possible to obtain patterns, especially millimeter-sized patterns, homogeneously over the entire head of hair, or in a localized manner on a part of the head of hair. These patterns may be imaginative from an aesthetic viewpoint or may serve to hide an irregularity in the colour or appearance of the keratin fibres, especially in the case of hair regrowth or fading of the ends.

Moreover, by using substrates comprising one or more oxidation dyes, i.e. substrates that are pretreated with a composition containing such dyes, this process makes it possible to reduce the risks of staining on the user's hands, scalp, face and/or clothing. Specifically, this process makes it possible to avoid the problems of running and/or errors in application of the dye compositions and oxidizing compositions.

Similarly, by means of applying such pretreated substrates, this process makes it possible to reduce the problem of shelf storage of the dye compositions and oxidizing compositions used in the standard processes, which makes it possible to substantially reduce the problems of space occupation. In particular, the user may have at his disposal a larger number of substrates pretreated with oxidation dyes while at the same time saving space in the hairstyling salons.

Moreover, the process according to the invention has the advantage of using pretreated substrates that can be satisfactorily stored over a period of time that may range, for example, from a few days to several months.

The oxidation dyeing process according to the invention also has the advantage of minimizing the risks of errors that may arise during the handling of the dye compositions and oxidizing compositions or in the choice of starting dye compositions so as to obtain the desired colouring.

The oxidation dyeing process according to the invention also makes it possible to obtain colourings and/or patterns whose colourings are powerful, sparingly selective and resistant with respect to external agents (such as shampoos, light, perspiration or bad weather).

In particular, the dyeing process according to the invention leads to the production of patterns whose colouring is powerful and resistant with respect to shampooing.

In particular, the substrate and the aqueous composition are successively applied on the keratin fibres.

The present invention also relates to a process for preparing a substrate containing on its surface one or more oxidation dyes, which consists in depositing, via a printing method chosen from a screen printing process and a printing process using an inkjet printer, a dye composition containing one or more oxidation dyes onto the surface of a substrate.

In other words, the dye composition is printed onto the surface of a substrate by means of a printing process so as to obtain a pretreated substrate.

The substrate obtained is thus surface-treated with the said composition based on oxidation dyes before being used in the oxidation dyeing process according to the invention.

The printing method which serves to deposit the composition onto the surface of a substrate may be a screen printing process, or a printing process using an inkjet printer.

This preparation process may be performed in the hairstyling salon itself, especially by means of the presence of an inkjet printer, before performing the oxidation dyeing process according to the invention.

The production of these pretreated substrates in the hairstyling salon itself and/or in the user's home has the advantage of minimizing the problems of storage, especially with regard to oxygen, since the user and/or the hairstylist will be able to use the substrates within minutes or hours of producing them.

Alternatively, this process may also be performed outside the hairstyling salon and as such the user merely has to use the substrates to dye the hair.

In this case, the pretreated substrate may be supplied to the user to produce a unified colouring and/or patterns on the hair.

The invention also relates to an element in sheet form pretreated on its surface with a composition comprising one or more oxidation dyes, the said composition being printed onto the surface of the element in sheet form and the said element further comprising at least one layer of at least one non-absorbing material.

In other words, another subject of the present invention relates to an element in sheet form comprising on its surface one or more oxidation dyes.

In particular, the element in sheet form comprises one or more oxidation dyes that have been printed onto its surface.

The element in sheet form according to the invention has the advantage of being easy to apply to locks of hair. In particular, such an element may be positioned with great precision at the place where it is desired to produce the coloured pattern(s) on the locks of hair.

The element in sheet form has the advantage of being able to be easily stored in the user's home when compared with the use of dye compositions used in standard oxidation dyeing processes, thereby making it possible to substantially reduce the space occupation.

Moreover, the element in sheet form may be prepared directly in the hairstyling salon or beforehand.

Other subject-matters and characteristics, aspects and advantages of the invention will become even more clearly apparent on reading the description and the examples which follow.

As indicated previously, the oxidation dyeing process uses on the said fibres a substrate that has been pretreated on its surface with a composition containing one or more oxidation dyes.

The substrate used in the process of the present invention is preferably dry.

According to the present invention, the term "dry" means that the substrate does not comprise volatiles solvents to less than 5 mg per cm$^2$, preferably less than 1 mg per cm$^2$ of the said substrate.

According to the present invention, the terms "volatiles solvents" mean that the solvents have a boiling temperature of less than 140° C.

The substrate may be in the form of an element in sheet form or in another embodiment.

According to a preferred embodiment, the substrate is an element in sheet form.

According to this preferred embodiment, the substrate is preferably a dry element in sheet form.

The element in sheet form may be made of plastic material, in particular thermoplastic, paper, a metal, especially aluminium, a woven, a nonwoven of non-absorbent fibres, especially of cellulose or a derivative thereof, or polyamide 6,6.

Preferably, the element in sheet form is a sheet of plastic material, especially of thermoplastic, or a nonwoven material of non-absorbent fibres, especially a nonwoven based on cellulose or a derivative thereof.

In particular, the element in sheet form used in the dyeing process is a plastic sheet.

The element in sheet form may consist of a water-soluble material, which makes it possible, for example, to remove it by washing the hair.

Preferably, the element in sheet form comprises an assembly of a layer of a water-soluble material and a layer of a non-water-soluble material, for example an aluminium foil.

The substrate may be designed to be able to be closed around a lock of hair. In this case, such a substrate is, for example, provided with a fastening means for keeping it in such a state, for example an adhesive disposed close to one edge or a mechanical attachment relief.

Preferably, the element in sheet form has a basis weight ranging from 20 to 300 g/m² and even more preferentially from 30 to 200 g/m².

The element in sheet form especially has a thickness ranging from 40 to 1000 micrometers, preferably a thickness ranging from 40 to 400 micrometers and better still from 60 to 200 micrometers.

The element in sheet form may be opaque or transparent. Preferably, the element in sheet form is transparent, which facilitates its positioning on the hair, especially when it is desired to produce one or more patterns at a precise place on the lock or on the head of hair. In other words, the transparency of the element in sheet form facilitates the implementation of the dyeing process, especially in the production of coloured patterns, and improves its precision.

The element in sheet form used in the dyeing process according to the invention is preferably flexible and strong. Preferentially, the strength of the sheet is greater than 300 kPa (standard TAPPI-T403).

Preferably, the element in sheet form is water-resistant. In particular, the water absorption of the said element is measured by the COBB 60 test which corresponds to the capacity of the said element to absorb water during contact for 60 seconds (the procedure of which is given by standard ISO 535, TAPPI-T411 measurement).

Thus, the element in sheet form absorbs less than 100 g/m² and preferentially less than 40 g/m² of water.

Preferably, the element in sheet form is resistant to the oily compounds. Thus, use may be made of a "food" paper, i.e. a complex of paper and of polymeric compound of the polyethylene type or of paper and paraffin, which is capable of acting as a barrier to water and to oils.

The element in sheet form may optionally be covered with a deposit of an adhesive composition. This adhesive layer makes it possible to improve the adhesion of the oxidation dye(s) to the surface of the element in sheet form.

According to a preferred embodiment, the element in sheet form, after treatment with the composition containing one or more oxidation dyes, may be covered with a protection means which serves to protect the surface of the said element from external elements. Thus, the element in sheet form comprises one or more oxidation dyes that may be covered with a protective layer. Such a protective layer makes it possible to minimize the impairment of the oxidation dye(s) caused by moisture, light or atmospheric oxygen.

Thus, the element in sheet form may be protected by implementing processes used in paper varnishing techniques (oil varnish, acrylic varnish, etc.), and in particular by using a water-based or organic acrylic varnish.

In this way, the element in sheet form containing one or more oxidation dyes may be surface-protected with a layer of acrylic varnish.

In accordance with this embodiment, the element in sheet form contains one or more oxidation dyes and is covered with a layer of acrylic varnish. In other words, the element in sheet form contains a layer containing one or more oxidation dyes and a layer of acrylic varnish, the two layers being juxtaposed one on the other.

The mass per unit area of the layer of acrylic varnish ranges from 1 to 10 g/m² and more particularly from 2 to 5 g/m².

According to one variant, the element in sheet form is covered with a detachable protective sheet. To do this, the edges of the element in sheet form and of the protective sheet are bonded together by means of a fastening means, especially an adhesive, which may be produced via any type of method, especially by heat sealing. Thus, good cohesion is ensured between the protective sheet and the element in sheet form.

Advantageously, the protective sheet is UV-opaque to ensure better protection.

According to another variant, the element in sheet form may be covered by another protective means, namely a hermetic wrapping, defining above the element a space without oxygen (under vacuum or under an inert atmosphere).

As indicated previously, the substrate comprises on its surface one or more oxidation dyes.

The oxidation dyes may be chosen from one or more oxidation bases, optionally in combination with one or more couplers. Preferably, the oxidation dyes comprise at least one oxidation base and at least one coupler.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis($\beta$-hydroxyethyl)-para-phenylenediamine, 4-N,N-bis($\beta$-hydroxyethyl)amino-2-methylaniline, 4-N,N-bis($\beta$-hydroxyethyl)amino-2-chloro aniline, 2-$\beta$-hydroxyethyl-para-phenylenediamine, 2-fluoro-para-phenylenediamine, 2-isopropyl-para-phenylenediamine, N-($\beta$-hydroxypropyl)-para-phenylenediamine, 2-hydroxymethyl-para-phenylenediamine, N,N-dimethyl-3-methyl-para-phenylenediamine, N-ethyl-N-($\beta$-hydroxyethyl)-para-phenylenediamine, N-($\beta,\gamma$-dihydroxypropyl)-para-phenylenediamine, N-(4'-aminophenyl)-para-phenylenediamine, N-phenyl-para-phenylenediamine, 2-$\beta$-hydroxyethyloxy-para-phenylenediamine, 2-$\beta$-acetylaminoethyloxy-para-phenylenediamine, N-($\beta$-methoxyethyl)-para-phenylenediamine, 4-aminophenylpyrrolidine, 2-thienyl-para-phenylenediamine, 2-$\beta$-hydroxyethylamino-5- aminotoluene, 3-hydroxy-1-(4'-aminophenyl)pyrrolidine, and the addition salts thereof with an acid.

Preference is particularly given, among the abovementioned para-phenylenediamines, to para-phenylenediamine, para-tolylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and the addition salts thereof with an acid.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof, described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethylamino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives, mention may be made of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives that may be mentioned are the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

Preferably, the oxidation bases are chosen from para-phenylenediamine, 1-methyl-2,5-diaminobenzene, para-aminophenol, 1-hydroxyethyl-4,5-diaminopyrazole sulfate and 2,3-diaminodihydroxypyrazolone dimethosulfonate, and mixtures thereof.

The coupler(s) are advantageously chosen from those conventionally used for the dyeing of keratin fibres.

Among these couplers, mention may be made especially of meta-phenylenediamines, meta-aminophenols, meta-diphenols, naphthalene-based couplers and heterocyclic couplers, and also the addition salts thereof.

Examples that may be mentioned include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and of the couplers that may be used in the context of the invention are especially chosen from addition salts with an acid such as hydrochlorides, hydrobromides, sulfates, citrates, succinates, tartrates, lactates, tosylates, benzenesulfonates, phosphates and acetates.

Preferably, the coupler(s) are chosen from resorcinol, 2-methylresorcinol, 5-N-(β-hydroxyethyl)amino-2-methylphenol, 2-methyl-5-aminophenol, 1-β-hydroxyethyloxy-2,4-diaminobenzene dihydrochloride and 3-aminophenol, and mixtures thereof.

The oxidation base(s) and optionally the coupler(s) may advantageously represent from 0.01% to 100% by weight, preferably from 1% to 50% by weight and better still from 5% to 40% by weight relative to the total weight of the treatment layer of the surface of the substrate.

The oxidation base(s) and optionally the coupler(s) may advantageously represent from 0.01% to 100% by weight, preferably from 1% to 50% by weight and better still from 5% to 40% by weight relative to the total weight of the composition for treating the surface of the substrate.

The oxidation dye(s) may be present on all or part of the surface of the substrate. Thus, the surface of the substrate may be entirely or partially covered with a layer containing one or more oxidation dyes.

Preferably, the oxidation dye(s) are deposited on a part of the surface of the substrate and represent patterns, which, after contact with the keratin fibres and the aqueous oxidizing composition, will make it possible to produce the coloured patterns on the said fibres. In other words, the oxidation dye(s) are deposited in the form of patterns on the surface of the substrate. Thus, the surface of the substrate comprises one or more oxidation dyes arranged in one or more particular geometrical forms, known as patterns, which, after reaction with the aqueous oxidizing composition, lead to the production of coloured patterns on the said fibres.

The pattern(s) may have any form, especially a geometrical form.

Thus, the dye(s) are present on a part of the surface of the substrate and represent patterns having the desired form.

The substrate may comprise, on the face opposite the face bearing the oxidation dye(s), a copy of the pattern(s) having the desired form. The production of these patterns on the opposite face makes it possible to indicate the place where the oxidation dye(s) may then be deposited on the surface of the substrate. Such a production facilitates thereafter the emplacement of the substrate on the keratin fibres at the place where it is desired to produce the pattern.

As a variant, such patterns are produced on the surface of the substrate before the pretreatment so as to deposit thereafter the oxidation dye(s) directly on the patterns. In other words, the patterns that it is desired to obtain on the keratin fibres may be produced beforehand on the surface of the substrate intended to be pretreated.

In both cases, the production of patterns on the surface of the substrate intended to be pretreated or on the surface opposite the pretreated surface is all the more advantageous when the substrate used is transparent.

In particular, the patterns may be printed beforehand on the substrate.

The substrate may also comprise on its surface one or more alkaline agents. In other words, the substrate may be pretreated with a dye composition comprising one or more oxidation dyes and one or more alkaline agents.

The alkaline agents may be chosen from carbonates, alkanolamines such as monoethanolamine, diethanolamine, triethanolamine and derivatives thereof, oxyethylenated and/or oxypropylenated ethylenediamines, mineral or organic hydroxides, alkali metal silicates such as sodium metasilicates, amino acids, preferably basic amino acids such as arginine, lysine, ornithine, citrulline and histidine, and the compounds of formula (I) below:

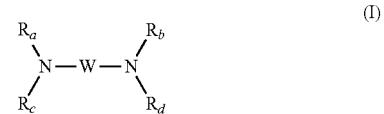

(I)

in which:

W is a divalent ($C_1$-$C_8$)alkylene group, preferably a propylene group, optionally substituted especially with a hydroxyl group or a $C_1$-$C_4$ alkyl radical;

$R_a$, $R_b$, $R_c$ and $R_d$, which may be identical or different, represent a hydrogen atom or a $C_1$-$C_4$ alkyl or $C_1$-$C_4$ hydroxyalkyl radical.

The mineral or organic hydroxides are preferably chosen from i) hydroxides of an alkali metal, ii) hydroxides of an alkaline-earth metal, for instance sodium hydroxide or potassium hydroxide, iii) hydroxides of a transition metal, such as hydroxides of metals from groups III, IV, V and VI, iv) hydroxides of lanthanides or actinides, quaternary ammonium hydroxides and guanidinium hydroxide.

The hydroxide may be formed in situ, for instance guanidine hydroxide, formed by reacting calcium hydroxide with guanidine carbonate.

In particular, the alkaline agents used are solid in the dry state.

In a first variant of the invention, the alkaline agents are solid before use in the dye composition, and are preferably chosen from carbonates, mineral hydroxides such as soluble sodium or potassium hydroxides or silicates.

In another variant of the invention, the alkaline agents are chosen from alkanolamines, in particular monoethanolamine, diethanolamine and triethanolamine.

The alkaline agent(s) may be present in a content ranging from 0.01% to 20% by weight relative to the total weight of the treatment layer of the surface of the substrate.

The alkaline agent(s) may be present in a content ranging from 0.01% to 20% by weight relative to the total weight of the treating dye composition of the surface of the substrate.

The dye composition may be aqueous or anhydrous.

When the dye composition is aqueous and contains one or more alkaline agents, the pH preferably ranges from 7.5 to 13, better still from 8 to 12 and even better still from 8 to 11.

The treating dye composition of the surface of the substrate may also comprise one or more antioxidant active agents, which are preferentially solid before use in the dye composition, such as ascorbic acid, cysteine or sulfites. The substrate may also comprise one or more compounds that are capable of slowing down the oxidative condensation reaction, such as acids, and in particular citric acid.

The active agent(s) may be present in a content ranging from 1% to 20% by weight relative to the weight of the oxidation dyes, both relative to the treatment composition and relative to the surface layer after pretreatment.

The dye composition may contain one or more organic solvents.

Organic solvents that may be mentioned include linear or branched and preferably saturated monoalcohols or diols, comprising 2 to 6 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol or propylene glycol monomethyl, monoethyl or monobutyl ether; and also diethylene glycol alkyl ethers, especially $C_1$-$C_4$ alkyl ethers, for instance diethylene glycol monoethyl ether or monobutyl ether.

The element may also comprise on the surface of the substrate a deposit of one or more activators or catalysts. In particular, the substrate comprises a deposit of one or more metal salts in a content ranging from 1% to 20% by weight relative to the weights of the oxidation dyes.

The substrate used in the dyeing process is pretreated with a dye composition containing one or more oxidation dyes.

Preferably, the substrate is pretreated with a dye composition containing one or more oxidation dyes and one or more alkaline agents.

The dye composition may be liquid or in powder form, preferably in liquid form.

The dye composition deposited on the surface of the substrate may optionally result from successive treatments of the substrate with one or more oxidation dyes, on the one hand, one or more alkaline agents, on the other hand, and optionally one or more active agents as described previously.

As indicated previously, the oxidation dyeing process uses an aqueous composition containing one or more chemical oxidizing agents.

The expression "chemical oxidizing agent" means an oxidizing agent other than atmospheric oxygen.

Preferably, the chemical oxidizing agent(s) are chosen from hydrogen peroxide, urea peroxide, alkali metal bromates or ferricyanides, peroxygenated salts, for instance alkali metal or alkaline-earth metal persulfates, perborates and percarbonates, and also peracids and precursors thereof.

More preferably still, the oxidizing agent(s) are chosen from hydrogen peroxide, urea peroxide or alkali metal bromates or ferricyanides.

This oxidizing agent advantageously consists of hydrogen peroxide, in particular in aqueous solution (aqueous hydrogen peroxide solution), the concentration of which may range more particularly from 0.1% to 50% by weight, even more preferentially from 0.5% to 20% by weight and better still from 1% to 15% by weight relative to the oxidizing composition.

Preferably, the oxidizing agents are chosen from hydrogen peroxide and/or persalts.

Preferably, the aqueous composition also contains one or more alkaline agents, especially the alkaline agents as described previously.

The use of an aqueous oxidizing composition containing one or more alkaline agents in the course of the dyeing process according to the invention makes it possible especially to lead to a lightening effect on the treated keratin fibres, which reinforces the visibility of the pattern(s) obtained with the oxidation dyes present on the surface of the substrate.

This use is particularly advantageous for dyeing dark or chestnut-brown hair.

The oxidizing aqueous composition may also comprise one or more colouring agents such as couplers.

In this way, placing in contact the keratin fibres, the pretreated substrate and the oxidizing aqueous composition containing one or more couplers will make it possible to lead to varied colourings, given that the coupler(s) present in the oxidizing composition will be able to react with the oxidation base(s) present on the substrate.

The use of an oxidizing aqueous composition containing one or more couplers is advantageous since it makes it possible to limit the use of the number of substrates by varying the nature of the oxidizing composition, while at the same time increasing the possible results as regards the colour.

The use of an oxidizing aqueous composition containing one or more couplers thus makes it possible to obtain a wide range of colours.

According to one embodiment, the oxidation dyeing process consists in placing the keratin fibres in contact with the substrate comprising on its surface one or more oxidation dyes, and in then applying to the said fibres the aqueous composition containing one or more oxidizing agents.

In particular, the keratin fibres are placed on the surface of the substrate bearing the oxidation dye(s), i.e. at the place where the surface of the substrate is covered with the oxidation dye(s), and the oxidizing aqueous composition is then applied to the said fibres. The oxidation dyes are thus dissolved, react with the oxidizing agent and dye the keratin fibres.

The oxidizing aqueous composition is especially applied using an applicator, in particular a brush, or by hand.

In accordance with this embodiment, after applying the oxidizing composition, the locks of hair thus treated may be protected with a paper to protect the other locks that have not been treated.

According to another embodiment, the oxidation dyeing process consists in applying an aqueous composition containing one or more oxidizing agents to the keratin fibres and then in applying to the said fibres a substrate comprising on its surface one or more oxidation dyes.

In this embodiment, the order of application between the pretreated substrate and the oxidizing aqueous composition is thus inverted relative to the preceding embodiment.

In this embodiment, the keratin fibres are especially placed on a support, for example the upper surface of a sheet of paper, the oxidizing aqueous composition is applied to the said fibres and the substrate pretreated with one or more oxidation dyes is then applied to the said fibres. The oxidation dyes present on the surface of the substrate are thus dissolved, react with the oxidizing agent and dye the covered keratin fibres.

In accordance with this embodiment, the substrate pretreated with one or more oxidation dyes is applied to the keratin fibres treated with the oxidizing aqueous composition so that the surface containing the oxidation dye(s) is in contact with the fibres.

This dyeing process referred to hereinbelow as the "reverse dyeing process" has the advantage of minimizing or even of eliminating the problems of contamination arising between the applicator used for applying the oxidizing composition and the oxidation dyes derived from the substrate.

Specifically, when the keratin fibres are first placed on the pretreated substrate, the applicator used for applying the oxidizing composition is then in contact with the oxidation dyes derived from the pretreated substrate which react with the oxidizing agents. Once the application has been performed, the applicator thus contains both oxidation dyes and the oxidizing aqueous composition, which has the consequence of entailing a risk of contamination of the rest of the oxidizing aqueous composition and of increasing the risks of impairing the colouring of the other keratin fibres.

In particular, when the applicator is a brush, its bristles contain oxidation dyes that have reacted with the oxidizing agents of the oxidizing composition. Consequently, the brush may impair the rest of the oxidizing composition, given that its bristles contain oxidation dyes.

The reverse dyeing process thus makes it possible to avoid this problem of contamination since the applicator does not come into contact with the oxidation dyes derived from the pretreated substrate. Thus, the rest of the oxidizing aqueous composition is not contaminated by the applicator and the risks of impairment of the colouring are minimized The reverse dyeing process is thus particularly advantageous.

Preferably, the oxidizing aqueous composition used in the reverse dyeing process also contains one or more alkaline agents.

The substrate pretreated with one or more oxidation dyes may be applied to the keratin fibres for a time ranging from 5 to 60 minutes and preferably ranging from 10 to 30 minutes.

The oxidizing aqueous composition may be applied to the keratin fibres for a time ranging from 5 to 60 minutes and preferably ranging from 10 to 30 minutes.

The substrate and the oxidizing aqueous composition may be applied at room temperature (25° C.), optionally with raising of the temperature, which may be up to 60° C.

After the treatment, the human keratin fibres are optionally rinsed with water, optionally washed with a shampoo and then rinsed with water, before being dried or left to dry.

Preferably, the substrate is pretreated with a dye composition containing one or more oxidation dyes and one or more alkaline agents and the oxidizing aqueous composition contains one or more oxidizing agents and optionally one or more alkaline agents.

The present invention also relates to a process for preparing the substrate as described previously, which consists in depositing, via a printing method chosen from a screen printing process or by means of a printing process using an inkjet printer, a dye composition containing one or more oxidation dyes onto the surface of a substrate.

In other words, the dye composition is printed onto the surface of a substrate so as to obtain a substrate containing on its surface one or more oxidation dyes.

Preferably, the dye composition comprises one or more oxidation dyes in a content ranging from 0.01% to 100% by weight, preferably from 1% to 50% by weight and better still from 5% to 40% by weight relative to the total weight of the said composition.

More preferentially, the dye composition comprises one or more oxidation dyes and one or more alkaline agents.

According to one embodiment, the process for preparing the substrate consists in depositing the composition containing the oxidation dye(s) onto the surface of a substrate covered with a deposit of an adhesive composition. This adhesive layer may cover all or part of the substrate. In particular, the adhesive layer may represent a pattern.

According to one embodiment, the process for preparing the substrate as described previously consists in partially depositing onto the surface of a substrate, via a printing method, a dye composition containing one or more oxidation dyes.

In accordance with this embodiment, the oxidation dye(s) are deposited in the form of one or more patterns onto the surface of a substrate.

In particular, the patterns may be squares, circles, ovals, ellipses or triangles, in the form of filled patterns or of lines surrounding these patterns.

They may also be thick or thin, straight or curved lines, crossed lines, representing letters, stylized drawings or geometrical patterns.

They may also be dotted lines or spots.

The printing method which serves to deposit the composition onto the surface of a substrate may be a screen printing process, or a printing process using an inkjet printer.

More preferentially, the composition containing one or more oxidation dyes is printed onto the surface of the substrate by means of an inkjet printer.

The composition containing the oxidation dye(s) may be liquid or may be in powder form.

When the preparation process consists in using a printing process using a laser printer, then the composition containing the oxidation dye(s) is in powder form.

In accordance with one embodiment, the process for preparing the substrate consists in depositing onto the surface of a substrate a composition containing the oxidation dye(s) and then in heating the said surface to fix the powder.

Preferably, the surface of the substrate is partially heated so as to create one or more patterns on the surface.

In accordance with another embodiment, the process for preparing the substrate consists in depositing the composition containing the oxidation dye(s) onto the surface of a substrate, and then in removing or rendering inefficient in certain places all or part of the oxidation dyes. In this way, this process can lead towards producing one or more patterns on the surface of the substrate.

The step consisting in partially removing the oxidation dye(s) may be performed by means of scraping, sponging, blowing, sucking or using an adhesive surface or a surface that is wetted at the places where it is desired to remove the oxidation dye(s).

The step consisting in rendering inefficient all or part of the oxidation dyes on the surface of the substrate may be performed by means of a chemical transformation, for example an oxidation or a reduction, or by covering with a protective compound.

Moreover, the process for preparing the substrate may also comprise a step that consists in applying a film of starch so as to reinforce the solidity of the substrate and improve the deposition of the oxidation dye(s) onto the surface of the substrate.

The film of starch may be thin, of the order of 2 g/m$^2$, or thick, of the order of 70 g/m$^2$.

The substrate thus pretreated in accordance with the preparation process according to the invention preferably dries within a period ranging from 5 minutes to 120 minutes, preferentially from 5 minutes to 90 minutes, more preferentially from 1 minute to 60 minutes and better still from 5 minutes to 60 minutes.

Advantageously, in this embodiment by printing, the substrate is an element in sheet form.

The invention also relates to an element in sheet form as described previously, which is pretreated on its surface with a composition comprising one or more oxidation dyes as described previously; the element in sheet form further comprises at least one layer of at least one non-absorbing material.

The element in sheet form is thus entirely or partially covered on its surface with one or more oxidation dyes.

The element in sheet form comprises on its surface one or more oxidation dyes.

In particular, the oxidation dye(s) have been printed onto the element in sheet form.

The element in sheet form may be made from a nonwoven fibre material, especially a nonwoven made of cellulose or a derivative thereof. In particular, the element in sheet form may be a paper of kraft type, which has the advantage of printing well and of leading to precise patterns. Specifically, the coloured patterns obtained on the keratin fibres do not run following the application of the oxidizing aqueous composition.

The element in sheet form may be a sheet of plastic material which especially has the advantage of rendering well the colouring power, which makes it possible to lead to patterns whose colouring is powerful. Furthermore, the sheet of plastic material does not absorb the water present in the oxidizing aqueous composition, which makes it possible to avoid creating dry areas under the keratin fibres during the application of the said composition.

Hence, the plastic material in the element in sheet corresponds to a non-absorbing material.

According to a first advantageous embodiment, the element in sheet form is a plastic sheet covered with a thin layer of paper, in particular with a thickness of less than 50 μm and more preferentially less than 30 μm, such as cigarette paper or a layer of paper that can be broken down in the presence of water, such as toilet paper, a thin layer of hydrophilic material such as cellulose or a hydrophilic silica.

According to this embodiment, the plastic sheet corresponds to the preferably non-absorbing material layer.

In accordance with this embodiment, the layer of thin paper allows rapid drying and prevents the colouring from running following the application of the oxidizing aqueous composition. Furthermore, the layer of paper located below the thin paper absorbs little or none of the oxidation dye(s) derived from the element in sheet form, as a result of its low thickness. The colouring is thus rendered well by the layer of thin paper on the keratin fibres, which leads especially to sharp coloured patterns. Furthermore, the element in sheet form in accordance with this embodiment makes it possible to minimize the dry areas under the keratin fibres.

When use is made of a support formed from a layer of paper, which is preferentially sparingly absorbent or non-absorbent, covered with a layer of paper that is capable of degrading on contact with water:

the layer of degradable paper (thickness possibly ranging from 10 to 200 μm) allows rapid drying and prevents the colouring from running following the application of the oxidizing aqueous composition. Furthermore, the layer of paper located below the degradable paper absorbs little or none of the oxidation dye(s) derived from the element in sheet form, as a result of its low thickness. The colouring is thus rendered well by the layer of thin paper on the keratin fibres, which leads especially to sharp coloured patterns. Furthermore, the element in sheet form in accordance with this embodiment makes it possible to minimize the dry areas under the keratin fibres.

In the case where a support formed from a layer of hydrophilic material is used:

the layer of hydrophilic material is typically from 5 to 200 μm thick, which allows rapid drying and prevents the colouring from running following the application of the aqueous composition. This especially results in sharp coloured patterns.

According to a second advantageous embodiment, the element in sheet form is a microalveolar sheet, i.e. a sheet perforated with holes that are spaced apart from each other by a plastic material. Thus, the oxidizing composition becomes housed in the holes of the substrate, which will make it possible to better render the power of the direct dyes on the keratin fibres after application of the aqueous composition.

The holes are found at the surface of the element in sheet form over a thickness ranging from 10% to 90% of the thickness of the sheet.

According to this embodiment, the plastic material corresponds to a non-absorbing material.

In accordance with this embodiment, the element in sheet form also has the advantage of printing well, of better rendering the colouring leading especially to powerfully coloured patterns, of not excessively absorbing the water originating from the aqueous composition and of minimizing the risks of running of the colouring, which results in precisely coloured patterns on the keratin fibres.

According to the first and second advantageous embodiments, the element in sheet form comprises at least one layer of at least one non-absorbing material.

Preferably, the said layer of at least one non-absorbing material is a plastic layer.

The following examples serve to illustrate the invention without, however, exhibiting a limiting nature.

EXAMPLE

Example 1

An inkjet printer is used. The cartridge is filled with a dye composition containing 30% by weight of 1-methyl-2,5-diaminobenzene. The dye composition also contains an alkaline agent in an amount such that the pH of the composition is equal to 9.

A pattern is printed on a plastic sheet, and the sheet is then reprinted so that its surface is treated with the dye composition.

The amount of the dye composition is 3 mg/cm$^2$ and 1 mg/cm$^2$ after drying.

The plastic sheet is then cut into a rectangle 18 cm long and 5 cm wide.

The plastic sheet is protected with a second plastic sheet.

An alkaline oxidizing aqueous composition is prepared by mixing weight-for-weight, at the time of use, the composition sold under the name Oxydant Riche INOA 30 volumes and the alkaline composition based on 10% by weight of monoethanolamine.

A hairstylist isolates a lock of his model's bleached hair using the technique of plaiting. He places the lock of hair on an aluminium foil. Next, he pastes the hair by applying the oxidizing aqueous composition to the lock with a brush, in an amount of 3 g. Next, he places the sheet prepared previously and using the edges of the aluminium foil to attach the plastic sheet.

The assembly is left to stand for 30 minutes. The two sheets are then removed and the lock is rinsed thoroughly. A shampoo is applied and the lock is then dried.

A coloured pattern (brown colour) is very clearly observed.

Example 2

The procedure of Example 2 is identical to that of Example 1, except that the alkaline oxidizing aqueous composition also comprises 1% by weight of 1-β-hydroxyethyloxy-2,4-diaminobenzene dihydrochloride.

A blue coloured pattern is very clearly observed.

Example 3

1. Compositions Tested

Compositions (A) to (F) below are prepared from the ingredients indicated below.

| | Composition A |
|---|---|
| 1-Methyl-2,5-diaminobenzene | 12 g (50% AM) |
| Water | qs 100 g |

| | Composition B |
|---|---|
| 1-β-Hydroxyethyloxy-2,4-diaminobenzene dihydrochloride | 12.5 g |
| Ethanol | 30 g |
| 2-Amino-2-methyl-1-propanol | qs pH = 10.3 |
| Water | qs 100 g |

| | Composition C |
|---|---|
| Resorcinol | 5.5 g |
| Ethanol | 10 g |
| Water | qs 100 g |

| | Composition D |
|---|---|
| 5(N-Hydroxyethyl)amino-o-cresol | 8.9 |
| Ethanol | 30 g |
| 2-Amino-2-methyl-1-propanol | qs pH = 10.3 |
| Water | qs 100 g |

| | Composition E |
|---|---|
| para-Aminophenol | 5.4 g |
| Ethanol | 40 g |

| | Composition E |
|---|---|
| 2-Amino-2-methyl-1-propanol | qs pH = 10.3 |
| Water | qs 100 g |

| | Composition F |
|---|---|
| 1-Methyl-2,5-diaminobenzene | 12 g (50% AM) |
| Water | qs 100 g |

2. Procedure

Compositions (A) to (F) are placed in the six compartments of an inkjet printer (Gatocopy).

Printing is then performed on a 5-square (3 cm×3 cm) inkjet printer transparency, selectively addressing the printer so that the following is printed on a square:

Square 1: composition (A)/composition (B) in a 50/50 weight ratio

Square 2: Composition (A)/Composition (C) in a 50/50 weight ratio

Square 3: Composition (A)/Composition (D) in a 50/50 weight ratio

Square 4: Composition (E)/Composition (D) in a 50/50 weight ratio

Square 5: Composition (F)/Composition (A)/Composition (B) in a 50/25/25 weight ratio After printing, the transparency appears tinted in the five printed squares.

Five locks of white hairs are placed on, spread out so as to cover the five squares.

An alkaline oxidizing aqueous composition is prepared from a weight-for-weight mixture, at the time of use, of a composition sold under the name Oxydant Riche INOA 30 volumes and of an alkaline composition based on 10% by weight of monoethanolamine.

The oxidizing aqueous composition is applied to each of the five locks of hair, in an amount of 8 g per lock. The assembly is left to stand for 30 minutes. The locks are removed from the transparency.

The locks are rinsed and then washed, and the formation of a strip is observed on each of the locks:

| | Colour of the locks |
|---|---|
| Lock 1 | Midnight blue |
| Lock 2 | Green-brown |
| Lock 3 | Violet-brown |
| Lock 4 | Light orange |
| Lock 5 | Mid-blue |

These patterns withstand washing well, especially after being washed six times.

Example 4

1. Compositions Tested

Compositions (G) to (J) below are prepared from the ingredients indicated below.

| | Composition G |
|---|---|
| 1-Methyl-2,5-diaminobenzene | 12 g (50% AM) |
| 1-β-Hydroxyethyloxy-2,4-diaminobenzene dihydrochloride | 12.05 g |

-continued

| | Composition G |
|---|---|
| Ethanol | 20 g |
| 2-Amino-2-methyl-1-propanol | qs pH = 10.3 |
| Water | qs 100 g |

Composition (H) is especially prepared from compositions (H') and (H") below:

| | Composition H' |
|---|---|
| 1-Methyl-2,5-diaminobenzene | 12.5 g (50% AM) |
| Resorcinol | 5.5 |
| Ethanol | 10 g |
| Water | qs 70 g |

| | Composition H" |
|---|---|
| Carbomer 980 | 1.5 g |
| 2-Amino-2-methyl-1-propanol | qs pH = 8 |
| Water | qs 30 g |

| | Composition I |
|---|---|
| para-Aminophenol | 5.4 g |
| 5(N-Hydroxyethyl)amino-o-cresol (Dragon Chemicals) | 8.9 g |
| Ethanol | 30 g |
| 2-Amino-2-methyl-1-propanol | qs pH = 10.3 |
| Water | qs 100 g |

2. Procedure

Compositions (G) to (I) are placed in the three compartments of an inkjet printer (Gatocopy), adjusting the ink feed so that it delivers 16 g/cm$^2$.

A square (3 cm×3 cm) is then printed on a sheet of ordinary paper of Kraft type for each composition.

After printing, the sheets of paper appear slightly tinted in the region of the printed squares.

The locks of hair (1 gram) are positioned, spread out on each sheet, on the printed squares.

An alkaline oxidizing aqueous composition is prepared from a weight-for-weight mixture, at the time of use, of a composition sold under the name Oxydant Riche INOA 30 volumes and of an alkaline composition based on 10% by weight of monoethanolamine.

The oxidizing aqueous composition is applied to each of the locks of hair, in an amount of 8 g per lock. The assembly is left to stand for 30 minutes. The locks are removed from the sheets.

The locks are rinsed and then washed, and the formation of a coloured strip is observed on each of the locks.

The invention claimed is:

1. A process for the oxidation dyeing of keratin fibers, the process comprising applying to the fibers:
   i) a substrate comprising on its surface a dye composition comprising at least one oxidation dye, wherein the dye composition is printed onto the surface of the substrate; and then
   ii) an aqueous composition comprising at least one chemical oxidizing agent and at least one alkaline agent.

2. The process according to claim 1, wherein the substrate is an element in sheet form.

3. The process according to claim 2, wherein the element in sheet form is made of plastic material, thermoplastic, paper, metal, aluminum, woven or nonwoven non-absorbent fibers, cellulose or derivatives thereof, or polyamide 6,6.

4. The process according to claim 2, wherein the element in sheet form comprises an adhesive layer on which are deposited at least one oxidation dye.

5. The process according to claim 1, wherein the at least one oxidation dye is chosen from oxidation bases and optionally comprises at least one coupler.

6. The process according to claim 5, wherein the oxidation bases are chosen from para-phenylenediamines, bis(phenyl) alkylenediamines, para-aminophenols, ortho-aminophenols, heterocyclic bases, 1-methyl-2,5-diaminobenzene, 1-hydroxyethyl-4,5-diaminopyrazole, 2,3-diaminodihydroxypyrazolone, the addition salts thereof, or mixtures thereof.

7. The process according to claim 5, wherein the couplers are chosen from meta-phenylenediamines, meta-aminophenols, meta-diphenols, naphthalene-based couplers, heterocyclic couplers, resorcinol, 2-methylresorcinol, 5-N-(β-hydroxyethyl)amino-2-methylphenol, 2-methyl-5-aminophenol, 1-β-hydroxyethyloxy-2,4-diaminobenzene dihydrochloride, 3-aminophenol, (5-N-hydroxyethyl)amino-o-cresol, 5-amino-ortho-cresol and 1-β-hydroxyethyloxy-2,4-diaminobenzene dihydrochloride, addition salts thereof, or mixtures thereof.

8. The process according to claim 1, wherein the at least one oxidation dye is present on a part of the surface of the substrate and represent patterns having the desired form.

9. The process according to claim 1, wherein the substrate comprises, on the face opposite the face bearing the at least one oxidation dye, a copy of at least one pattern.

10. The process according to claim 1, wherein the surface of the substrate comprises, prior to the deposition of the at least one oxidation dye, at least one pattern.

11. The process according to claim 1, wherein the substrate is transparent.

12. The process according to claim 11, wherein the substrate further comprises on its surface at least one alkaline agent.

13. The process according to claim 1, wherein the aqueous composition comprises at least one oxidizing agent.

14. The process according to claim 1, wherein the aqueous composition further comprises at least one coloring agent or coupler.

15. The process according to claim 1, comprising preparing the substrate by depositing, via a printing method chosen from a screen printing process or a printing process using an inkjet printer, a composition containing at least one oxidation dye onto the surface of the substrate.

16. An element in sheet form, pretreated on a surface with a composition comprising at least one oxidation dye and at least one layer of at least one non-absorbing material; wherein:
   the composition is printed on the surface of the element in sheet form, and
   the element in sheet form is chosen from a plastic sheet covered with a layer of paper having a thickness of less than about 50 μm or a layer of hydrophilic material having a thickness ranging from about 5 μm to about 200 μm.

17. The element in sheet form according to claim 16, wherein the element is sheet form is a microalveolar sheet wherein the holes are spaced apart from each other by a plastic material.

* * * * *